(12) United States Patent
Robinson et al.

(10) Patent No.: US 11,406,845 B2
(45) Date of Patent: Aug. 9, 2022

(54) NON-INVASIVE IMAGING AND TREATMENT SYSTEM FOR CARDIAC ARRHYTHMIAS

(71) Applicant: Washington University, St. Louis, MO (US)

(72) Inventors: Clifford G. Robinson, Chesterfield, MO (US); Phillip S. Cuculich, St. Louis, MO (US)

(73) Assignee: Washington University, St. Louis, MO (US)

( * ) Notice: Subject to any disclaimer, the term of this patent is extended or adjusted under 35 U.S.C. 154(b) by 531 days.

(21) Appl. No.: 15/773,415

(22) PCT Filed: Nov. 7, 2016

(86) PCT No.: PCT/US2016/000103
§ 371 (c)(1),
(2) Date: May 3, 2018

(87) PCT Pub. No.: WO2017/078757
PCT Pub. Date: May 11, 2017

(65) Prior Publication Data
US 2018/0318606 A1 Nov. 8, 2018

Related U.S. Application Data

(60) Provisional application No. 62/252,104, filed on Nov. 6, 2015.

(51) Int. Cl.
*A61N 5/10* (2006.01)
*A61B 5/05* (2021.01)
(Continued)

(52) U.S. Cl.
CPC ............ *A61N 5/1039* (2013.01); *A61B 6/503* (2013.01); *A61B 6/5247* (2013.01);
(Continued)

(58) Field of Classification Search
CPC ...... A61N 5/1039; A61N 5/10; A61N 5/1068; A61N 5/1083; A61B 6/503; A61B 6/5247; A61B 8/5261; A61B 18/00
See application file for complete search history.

(56) References Cited

U.S. PATENT DOCUMENTS

| | | |
|---|---|---|
| 5,311,873 A | 5/1994 | Savard et al. |
| 7,346,381 B2 | 3/2008 | Okerlund et al. |

(Continued)

FOREIGN PATENT DOCUMENTS

| | | |
|---|---|---|
| CN | 1820802 A | 8/2006 |
| CN | 101199416 A | 6/2008 |

(Continued)

OTHER PUBLICATIONS

Accuray Incorporated, "DICOM Conformance Statement for Accuray Cyberknife® System", Nov. 15, 2007, pp. 1, 5, http://www.jira-net.or.jp/dicom/file/dicom_cs_cyberknife.pdf, Accessed Dec. 30, 2016.
(Continued)

*Primary Examiner* — Michael W Kahelin
*Assistant Examiner* — Pamela M. Bays
(74) *Attorney, Agent, or Firm* — Armstrong Teasdale LLP

(57) ABSTRACT

Disclosed are systems and methods for the treatment of cardiac arrhythmias.

9 Claims, 10 Drawing Sheets

(51) Int. Cl.
*A61B 18/00* (2006.01)
*A61B 6/00* (2006.01)
*A61B 8/08* (2006.01)
A61B 6/03 (2006.01)
A61B 5/055 (2006.01)
A61N 5/00 (2006.01)
A61N 1/39 (2006.01)
A61B 5/282 (2021.01)
A61B 5/318 (2021.01)

(52) U.S. Cl.
CPC ............ *A61B 8/5261* (2013.01); *A61B 18/00* (2013.01); *A61N 5/10* (2013.01); *A61N 5/1068* (2013.01); *A61N 5/1083* (2013.01); A61B 5/055 (2013.01); A61B 5/282 (2021.01); A61B 5/318 (2021.01); A61B 6/032 (2013.01); A61B 8/0883 (2013.01); A61B 8/483 (2013.01); A61B 8/488 (2013.01); A61B 2576/023 (2013.01); A61N 1/39 (2013.01); A61N 5/00 (2013.01)

(56) References Cited

U.S. PATENT DOCUMENTS

| | | | |
|---|---|---|---|
| 8,086,010 | B2 | 12/2011 | Nabatame et al. |
| 8,849,633 | B2 | 9/2014 | Core et al. |
| 9,370,312 | B2 | 6/2016 | Schwartz |
| 9,427,166 | B2 | 8/2016 | Dubois et al. |
| 10,292,588 | B2 | 5/2019 | Ben-Haim et al. |
| 2002/0128565 | A1* | 9/2002 | Rudy ................... A61B 5/6855 600/509 |
| 2003/0187358 | A1* | 10/2003 | Okerlund ............... G16H 50/50 600/443 |
| 2007/0083108 | A1* | 4/2007 | Boese ................... A61B 90/36 600/426 |
| 2007/0153969 | A1* | 7/2007 | Maschke ................ A61B 6/547 378/4 |
| 2012/0035459 | A1* | 2/2012 | Revishvili .............. A61B 6/032 600/411 |
| 2013/0102896 | A1* | 4/2013 | Sumanaweera ...... A61N 5/1031 600/427 |
| 2013/0184697 | A1 | 7/2013 | Han et al. |
| 2013/0267828 | A1 | 10/2013 | Jerosch-Herold et al. |
| 2014/0088395 | A1 | 3/2014 | Dubois et al. |
| 2015/0320515 | A1* | 11/2015 | Edwards ............... A61B 8/4254 600/389 |

FOREIGN PATENT DOCUMENTS

| | | |
|---|---|---|
| CN | 103202727 A | 7/2013 |
| CN | 104027106 A | 9/2014 |
| CN | 104936511 A | 9/2015 |
| EP | 2897522 A1 | 7/2015 |
| WO | 2004062479 A2 | 7/2004 |
| WO | 2008086430 A1 | 7/2008 |
| WO | 2008115830 A2 | 9/2008 |
| WO | 2009042842 A1 | 4/2009 |
| WO | 2011009121 A1 | 1/2011 |

OTHER PUBLICATIONS

International Preliminary Report on Patentability (Chapter II) for PCT/US2016/000103 dated Mar. 29, 2018.
Burnes et al., "A Noninvasive Imaging Modality for Cardiac Arrhythmias", Circulation, Published Oct. 24, 2000, pp. 2152-2158, vol. 102, No. 17.
Dubois et al., "Non-Invasive Cardiac Mapping in Clinical Practice: Application to the Ablation of Cardiac Arrhythmias", J Electrocardiol., Published Aug. 15, 2015, pp. 966-974, vol. 48., No. 6.
Li et al., "Localization of the Site of Origin of Cardiac Activation by Means of a Heart-Model-Based Electrocardiographic Imaging Approach", IEEE Trans Biomed Eng., Published Jun. 2001, pp. 660-669, vol. 48, No. 3.
Loo et al., "Stereotactic Ablative Radiotherapy for the Treatment of Refractory Cardiac Ventricular Arrhythmia", Circ Arrhythm Electrophysiol, Published Jun. 1, 2015, pp. 748-750, vol. 8., No. 3.
Shah et al., "Body Surface Electrocardiographic Mapping for Non-Invasive Identification of Arrhythmic Sources", Arrhythm Electrophysiol Rev., Published Apr. 2013, pp. 16-22, vol. 2, No. 1.
Wang et al., "Application of the Method of Fundamental Solutions to Potential-Based Inverse Electrocardiography", Ann Biomed Eng., Published Jun. 29, 2006, pp. 1272-1288, vol. 34, No. 8.
Wang et al., "Focal Atrial Tachycardia after Pulmonary Vein Isolation: Noninvasive Mapping with Electrocardiographic Imaging (ECGI)", Heart Rhythm, Published May 4, 2007, pp. 1081-1084, vol. 4, No. 8.

* cited by examiner

NON-INVASIVE IMAGING AND TREATMENT SYSTEM FOR CARDIAC ARRHYTHMIAS

CROSS-REFERENCE TO RELATED APPLICATIONS

The present application is a PCT U.S. National Phase application of PCT/US2016/000103, filed on Nov. 7, 2016, which claims the benefit of U.S. Provisional Patent Application Ser. No. 62/252,104, filed Nov. 6, 2015 which are incorporated herein by reference in their entirety. This invention was made with government support under NIH R01 HL03334331 Awarded by the National Institutes of Health. The government has certain rights in the invention.

I. BACKGROUND

The present invention is generally related to treatment of arrhythmia, and in one embodiment provides a non-invasive method for imaging and treatment of arrhythmia having long-term efficacy.

Sudden cardiac arrest (SCA) is the single largest cause of death in the developed world. In the United States, over 325,000 deaths are due to SCA; more than lung cancer, breast cancer and AIDS combined. A majority of SCA is due to cardiac arrhythmias, namely ventricular tachycardia (VT). Underlying cardiomyopathies and scarring most often cause ventricular arrhythmias. The scar from the cardiomyopathy (i.e., previous heart attack) forms the substrate for abnormal electrical circuits within the heart, which causes VT. Survival from an out-of-hospital SCA is only 10%. Patients who survive SCA have an estimated 40-60% chance of developing another ventricular arrhythmia in the subsequent year.

A typical adult human heart beats between 60-100 beats per minute. An arrhythmia is any heart rhythm that is not the normal sinus rhythm with normal conduction through the atrioventricular node. Arrhythmias can be generally categorized as bradycardia (very slow heart rate) or tachycardia (very fast heart rate). Clinically, tachycardias represent the largest group, and can generally be divided into supraventricular (i.e. supraventricular tachycardia, premature supraventricular contractions, atrial fibrillation, atrial flutter, etc.) or ventricular (ventricular tachycardia, ventricular fibrillation, premature ventricular contractions, etc.).

Arrhythmias interfere with the heart's ability to pump blood, and can result in severe symptoms, including, but not limited to, palpitations, congestive heart failure, ischemia, embolism (stroke, pulmonary embolism), and sudden death. Arrhythmias affect millions of people throughout the world, and are a major cause of morbidity and mortality.

Goals of care include improving symptoms and attempting to prevent a life-threatening outcome. Based on symptoms, severity, and cause of the arrhythmia, treatment options include, but are not limited to, antiarrhythmic drugs, placement of a pacemaker/defibrillator, surgical ablation, catheter-based ablation (endocardial, epicardial) using radiofrequency energy to create thermal injury), and/or a combination thereof.

Invasive catheter-based ablation is the contemporary management for most arrhythmias that remain refractory to medical therapy. These procedures are performed worldwide, and consist on insertion of several long, thin catheters into the heart percutaneously through large veins or arteries in the groin or neck. Successes and risks of this type of procedure range widely, based on the type of arrhythmia, complexity of the arrhythmia mechanism, invasiveness of the mapping, duration of the procedure, underlying patient comorbid conditions, and natural history of the underlying cardiac disease. Failure of a procedure can happen for many reasons, including limitations to invasive mapping, limitations to invasive ablation, development of different arrhythmias after the index ablation, etc. Broadly, the risks of an invasive catheter ablation also range, with lower risks for the most commonly performed procedures (1% major complication, 8% minor complication) and significantly higher risks for complex procedures (6-8% major complication, 10+% minor complication).

In addition to the invasive application of a treatment, current treatment protocols utilize invasive visualization techniques to direct the application of the treatment. What are needed are treatments that utilize both noninvasive visualization and noninvasive delivery of a therapeutic.

II. SUMMARY

Disclosed are methods and compositions related to a system for treating cardiac arrhythmia comprising an entirely noninvasive means for imaging an arrhythmia and an entirely noninvasive means for treating a heart (i.e., a catheter-free, electrophysiology (EP)-guided noninvasive cardiac radioablation (ENCORE) system).

Also disclosed are catheter-free, electrophysiology (EP)-guided noninvasive cardiac radioablation (ENCORE) methods of treating cardiac arrhythmia comprising computing heart electrical activity data from a set of noninvasively measured body surface electrical potentials; obtaining a patient's heart-torso geometry using a non-invasive imaging modality; generating a co-registered map of the heart's electrical activity and the heart's anatomy; determining one or more target treatment regions using the co-registered map; and directing a noninvasive therapy to the one or more target regions.

In one aspect, the disclosed methods and systems can comprise a processor configures to allow the user to define the arrhythmia target using electophysicolgical (for example, ECGI) data overlaid on a CT image set of a patient's torso and then translate the defined target on the CT image set back into CT slices that can be imported into any DICOM compliant treatment planning system (TPS). These images can subsequently be co-registered to the primary planning CT dataset per standard treatment planning, and used to define the arrhythmia target on the primary planning CT dataset.

In another aspect, the method and systems can comprise a processor configured to allows the user to define the arrhythmia target using ECGI data, reconstruct that target as a DICOM-RT compliant structure registered to the ECGI CT, and then exported as a DICOM-RT structure set with reference CT. These DICOM-RT compliant files can then be imported into any DICOM compliant treatment planning system (TPS). These images can be subsequently co-registered to the primary planning CT dataset and the target as defined in the structure set re-mapped or transferred to the primary planning CT dataset using standard tools available in all TPS.

In another aspect, the method and systems can comprise a processor that allows the user to define the arrhythmia target using ECGI data, reconstruct that target as a DICOM-RT compliant dose object registered to the ECGI CT, and then exported as a DICOM-RT dose with reference CT. These DICOM-RT compliant files can then be imported into any DICOM compliant treatment planning system (TPS).

These images can be subsequently co-registered to the primary planning CT dataset and the target as defined by the dose cloud used to define a target in the TPS.

In another aspect, the methods and systems disclosed herein can comprise a processor that allows the user to define the arrhythmia target using ECGI data in real-time while the patient is on the machine, and direct therapy to the target using the ECGI data.

III. BRIEF DESCRIPTION OF THE DRAWINGS

The accompanying drawings, which are incorporated in and constitute a part of this specification, illustrate several embodiments and together with the description illustrate the disclosed compositions and methods.

Figure 3A:
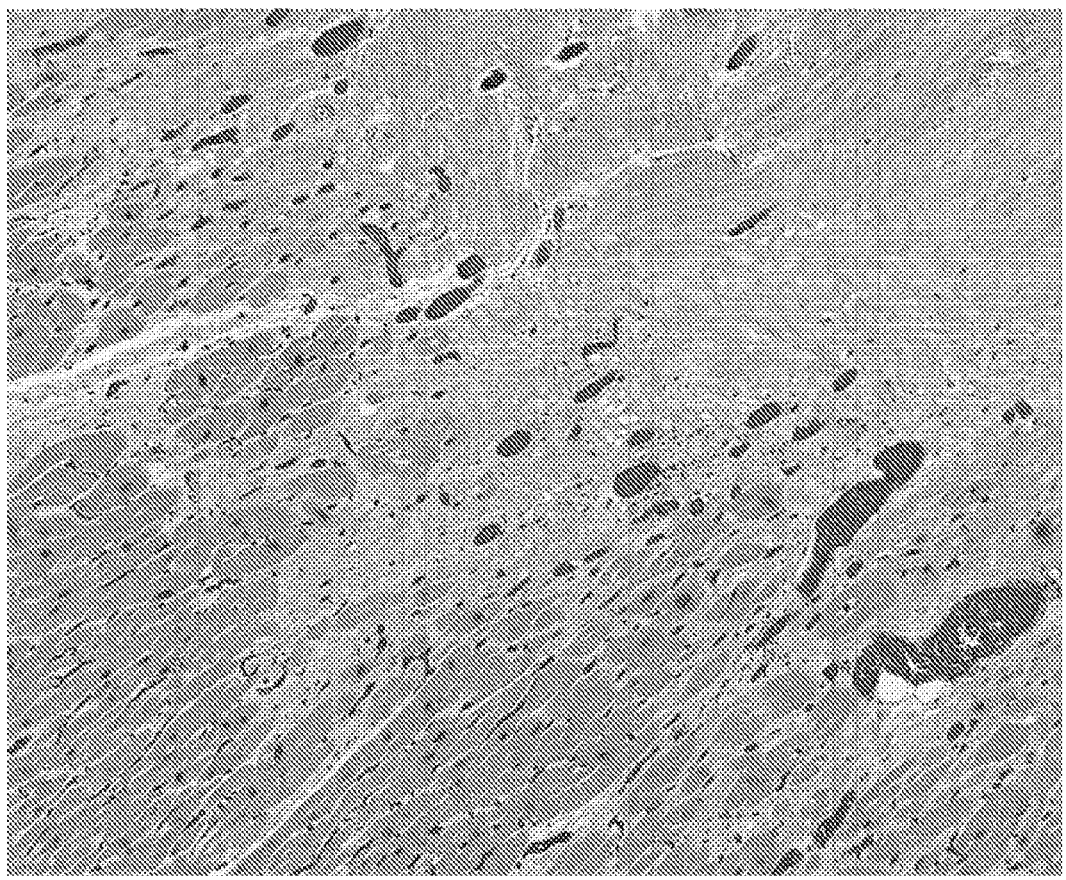
FIG. 3A shows a hematoxylin and eosin stain of targeted myocardium with subendocardial fibrosis from the prior infarction (upper right) and prominent small vessel ectasia at the interface of fibrosis and viable myocardium. The absence of myocardial inflammation/necrosis is noted. (200×, H&E)
Figure 3B:
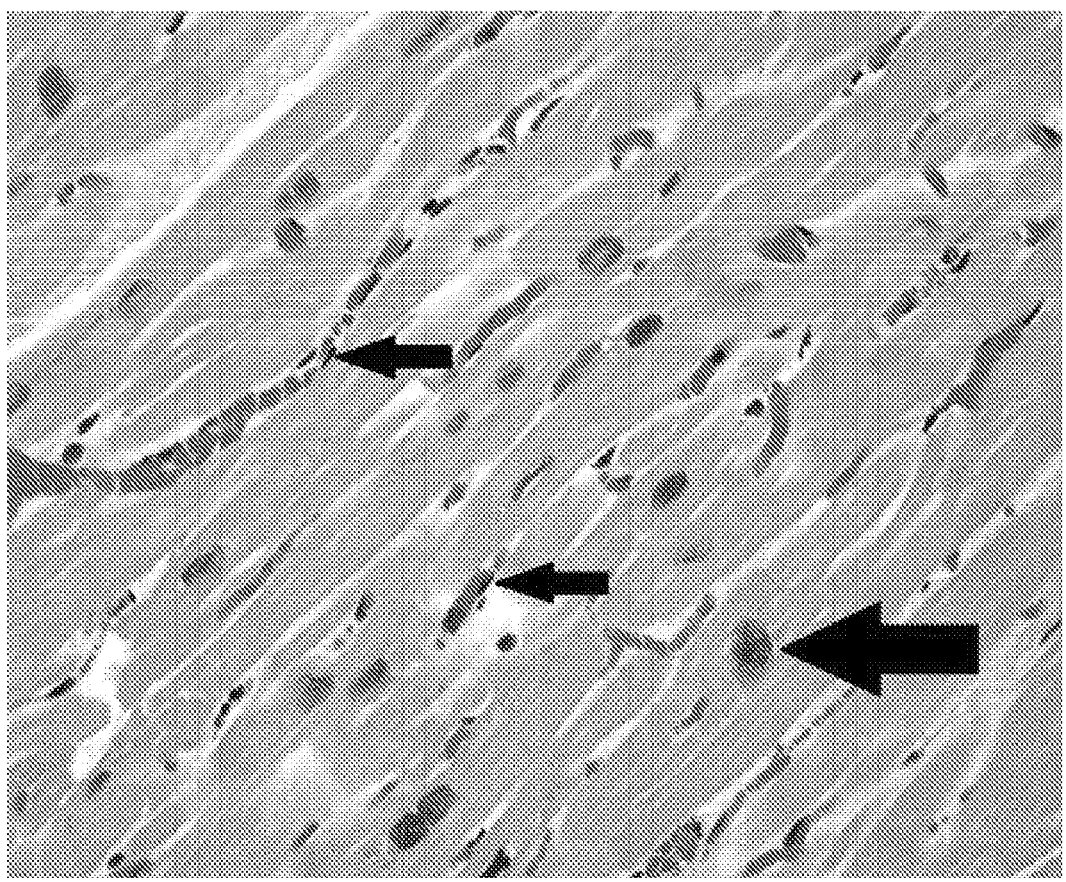

FIG. 3B shows a hematoxylin and eosin stain of myocardium within the targeted field. Hypertrophic cardiomyocytes with large rectangular nuclei, so called "boxcar nuclei" (large arrow) and surrounding dilated arterioles and venules. Endothelial cells are normal in appearance (small arrows), showing thin and elongated, non-reactive nuclei. Yellow/brown lipofuscin pigment is seen at the poles of myocyte nuclei, considered normal for a patient of this age. (400×, H&E).

Figure 4:
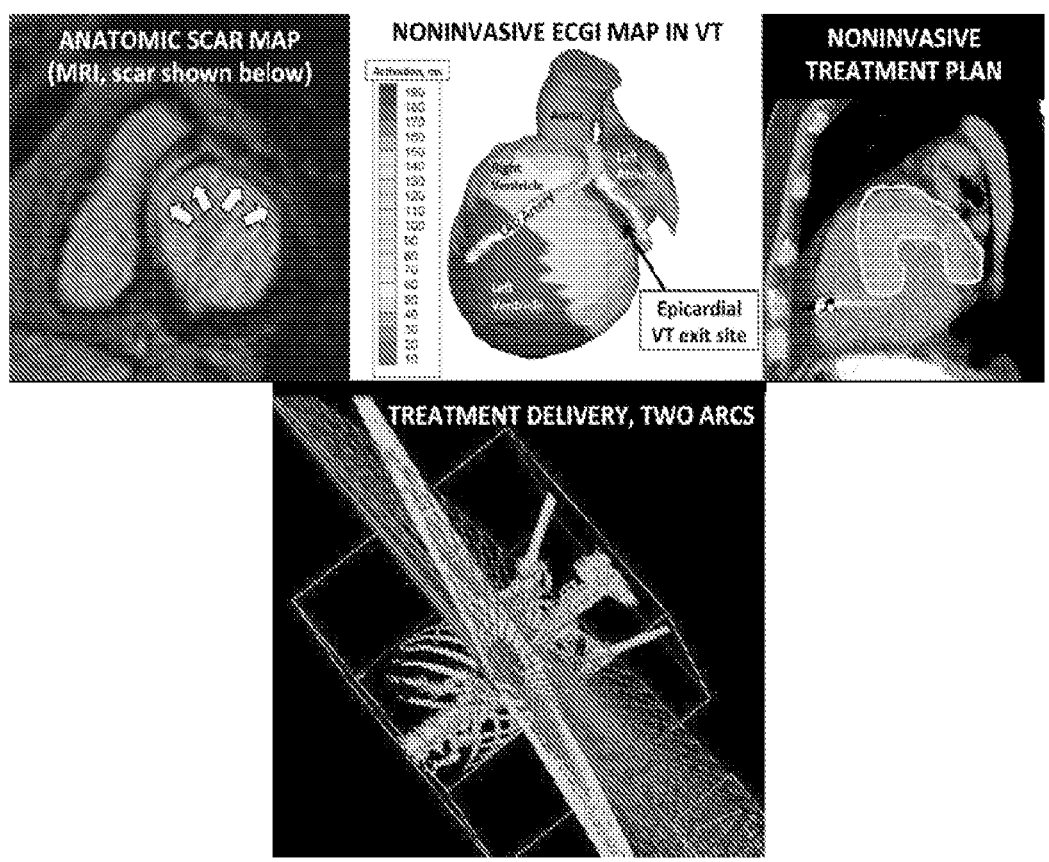

FIG. 4 shows the ENCORE procedure treatment plan. TOP LEFT—Cardiac MRI demonstrating the extensive mid-myocardial scar (yellow arrows); TOP MIDDLE—Noninvasive electrical mapping (ECGI) performed during VT; TOP RIGHT—Noninvasive ablation treatment plan (light green is target volume) combining electrical and anatomic information; BOTTOM—Stereotactic radiotherapy delivered with 2 VMAT noncoplanar arcs to 25 Gy/single fraction. As such, the delivery methods within this protocol are novel inasmuch as they are 1) rapid; 2) entirely non-invasive; 3) guided by noninvasive imaging of the electrical and structural abnormalities.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Current standard of care treatment for medically-refractory cardiac arrhythmias often involves an invasive catheter-based ablation procedure that targets the arrhythmogenic tissue. This procedure generally takes 4-8 hours, often uses general anesthesia, and requires access to the inside of the heart through the veins or arteries of the leg or access to the outside of the heart through the skin underneath the breastbone. Long flexible catheters are inserted and maneuvered to identify critical components of the abnormal electrical circuit that causes VT. Once identified, radiofrequency energy is applied to the tip of the catheter (usually 3.5 mm tip) to heat up the critical tissue to the point of cellular destruction (ablation), thus rendering it electrically inert. These critical components of the circuit are often located within abnormal cardiac tissue, most commonly from previous myocardial infarctions.

This procedure carries risks related to the invasive nature of introducing several catheters into the heart (bleeding at venipuncture sites), risks related to thermal injury during ablation (including perforation of the heart), risks related to prolonged anesthesia (as long as 8-10 hours). This risks can result in death (3%), stroke/transient ischemic attack (1-2%), cardiac perforation (1-2%), third-degree heart block (1.6%), pericardial effusion/tamponade (1%), worsening heart failure and cardiogenic shock (1-2%), uncontrollable VT (1%), and sepsis (<1%). In the case of a particular arrhythmia, ventricular tachycardia, the success rate of the invasive ablation is approximately 50% with a 3% procedure-related mortality rate and a >7% procedure-related complication rate. Improvement on the current standard of care would involve 1) better success rates; 2) shorter procedures with 3) less risk.

Currently, noninvasive diagnosis is based on the standard 12-lead ECG, which measures electrical potentials (electrocardiograms) on the body surface, far away from the heart. Due to the limited number of leads and their distance from the heart's surface, ECG is severely limited in resolution and lacks in sensitivity and specificity.

Figure 1A:
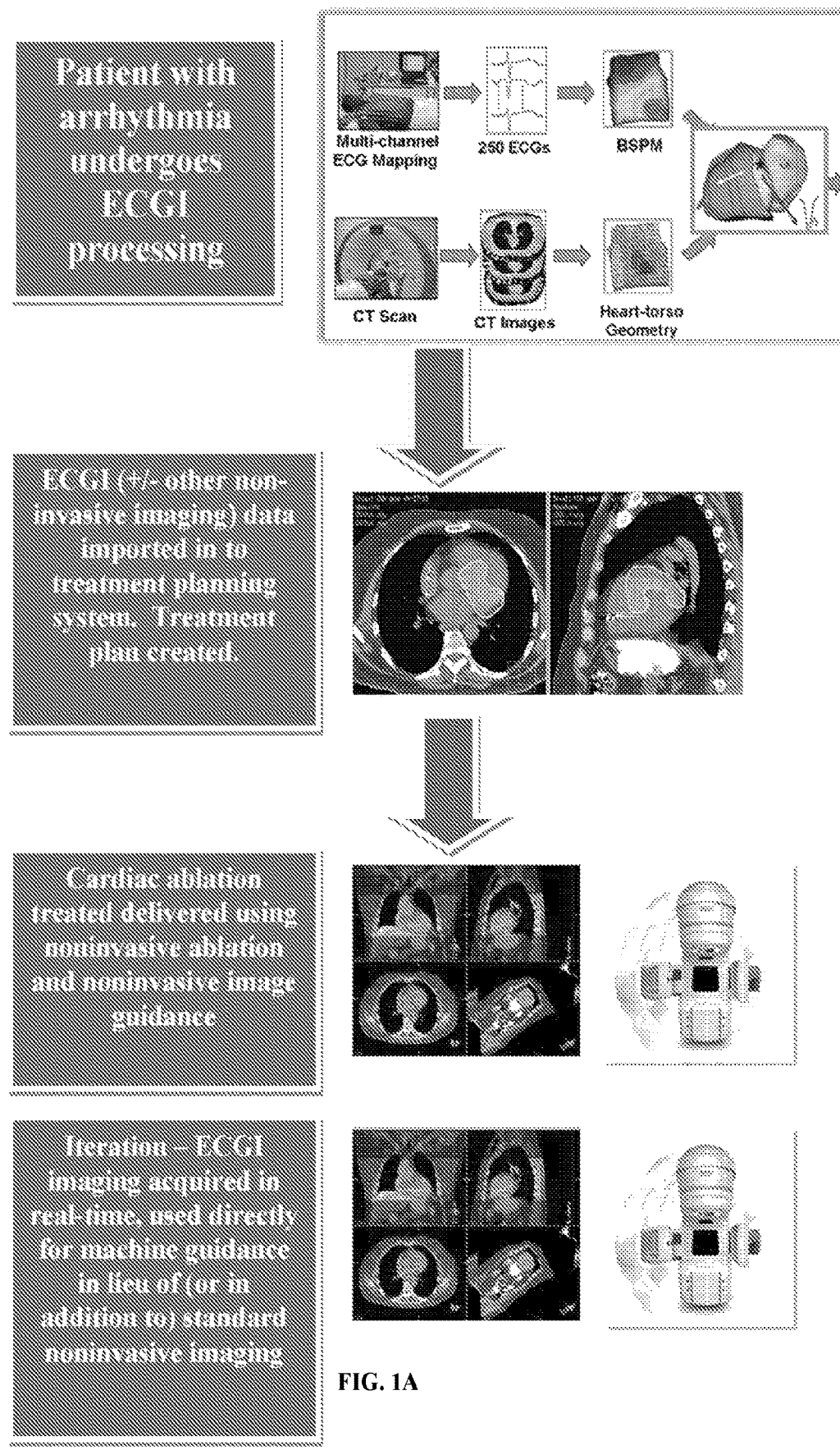
FIG. 1A shows an exemplary illustration of an integrated Electrocardiographic Imaging and radiotherapy system and its implementation.
Figure 1B:
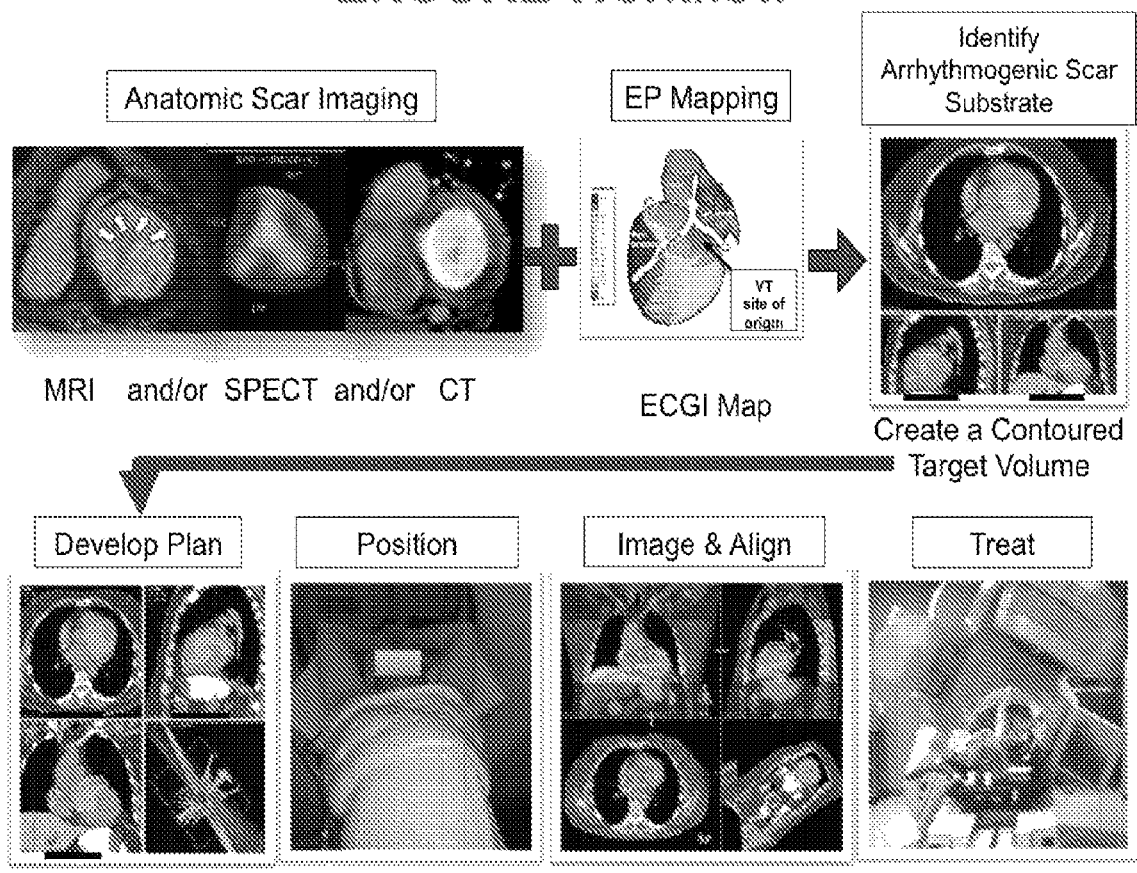
FIG. 1B shows one iteration of an exemplary illustration of an integrated Electrocardiographic Imaging and radiotherapy system and its implementation

Thus there is a need for use of currently existing technology for delivery of noninvasive radiotherapy (including, but not limited to ablative doses of radiation) to targets in the body (stereotactic cardiac ablation) for purposes of arrhythmia treatment. There is also a need for noninvasive imaging to accompany the noninvasive treatments. Presently, there are no methods allowing a purely noninvasive electrophysiologic targeting AND treatment of cardiac arrhythmias. The merging of noninvasively-acquired, high-fidelity, data with a noninvasive treatment delivery using radiotherapy represents a novel and potentially practice changing application of both technologies. Accordingly, in one aspect disclosed herein are noninvasive systems for imaging and treating cardiac arrhythmia in a subject comprising a noninvasive means for imaging an arrhythmia and a noninvasive means for treating said arrhythmia as exemplified by FIGS. 1A and 1B.

It is understood and herein contemplated that prior to treatment an image of the target can be created to direct the treatment to the appropriate area. Previous reports of stereotactic cardiac radiosurgery in animals and humans have required the use of invasive (catheter-based), low-fidelity electrical tests (12-lead ECG) or noninvasive anatomic information (nuclear cardiac scan) information regarding location and size of the arrhythmia focus for radiosurgery targeting. Disclosed herein are methods comprising noninvasive imaging of an arrhythmia for purposes of noninvasive treatment (including, but not limited to stereotactic cardiac ablation). As used herein, "imaging" can refer to interrogate either the electrophysiological signatures of arrhythmia, the anatomical signatures of arrhythmia, or both. It is understood that there can be many equally sufficient methods for noninvasively imaging a heart and an arrhythmia which can be used alone or in conjunction including but not limited to electrocardiographic imaging (ECGI), magnetic resonance imaging (MRI), nuclear medicine studies (PET, SPECT), computed tomography (CT) scanning, cardiac ultrasonography, or any other noninvasive imaging technique known. Thus, for example, in one aspect, disclosed herein are noninvasive systems for imaging and treating cardiac arrhythmia in a subject comprising a noninvasive means for imaging an arrhythmia and a noninvasive means for treating said arrhythmia, wherein the noninvasive imaging means comprises one or more of electrocadiagraphic imaging, magnetic resonance imaging, cardiac computed tomography, cardiac nuclear medicine, cardiac ultrasonoagraphy, and ECVUE. In one aspect, the disclosed systems and methods can comprise a noninvasive imaging means comprising) ECGI alone; b) ECGI in conjunction with other anatomic imaging; c) anatomic imaging alone (where the electrical and anatomic signatures of arrhythmia may be determined without the need to map the actual arrhythmia).

Electrocardiographic Imaging (ECGI) is an important development toward improving four-dimensional precision of imaging cardiac electrophysiology. As used herein, "electrocardiographic imaging" (ECGI) refers to a technique which reconstructs epicardial potentials, electrograms, and activation sequences (isochrones) from electrocardiographic body-surface potentials noninvasively. In brief, the patient undergoes a CT or MRI scan while wearing a vest of electrodes that record electrical activity. The major electrical activity signal is from cardiac electrical activity. The electrical information from the surface of the body can then be registered to a patient-specific heart model derived from CT or MRI images to display the characteristics of the cardiac electrical activity mapped onto a patient's anatomy. Useful information includes: where the heart beat begins, the depolarization sequence of the heart tissue, and which parts of the heart have abnormal depolarization behavior. Fitting the vest of electrodes on the patient, obtaining electrical data, and performing the CT scan is generally completed in under 30 minutes.

The technique addresses solving of the electrocardiographic inverse problem, which due to computation of epicardial potentials from body surface potentials can result in significant errors. Regularization methods (typically Tikhonov regularization or the generalized minimal residual (GMRes) method) are used to minimize error. Typically ECGI utilizes (i) electrocardiographic unipolar potentials measured over the entire body surface (BSPs) and (ii) the heart-torso geometrical relationship. In one aspect, ECGI can utilize an electrode vest strapped to the subject's torso and connected to a multichannel mapping system measured BSP. The vest can include at least 50, 60, 70, 80, 90, 100, 110, 120, 130, 140, 150, 160, 170, 180, 190, 200, 210, 220, 230, 240, 250, 260, 270, 280, 290, or 300 or more electrodes to measure BSP. ECGI incorporates the patient-specific anatomy of the heart with the recording leads on the body surface to noninvasively reconstruct the electrical activity on a three-dimensional model of the patient's heart surface. As used herein ECGI is understood to include other electrocardiographic mapping (ECM) platforms ECVUE, noninvasive epicardial and endocardial electrophysiology system (NEEES), Noninvasive Imaging of Cardiac Electrophysiology (NICE) or any other iteration that uses mathematical solutions for the inverse problem of electrocardiography, which uses potentials measured at the surface of the body and reconstructs them onto the a model of the surface of the heart.

As used herein, "magnetic resonance imaging" refers to the use of use magnetic fields and radio waves to form images of the body. Typically, when used in cardiac situations, cardiovascular magnetic resonance imaging (CMR) involves ECG gating which combats the artifacts created by the beating of the heart.

"Cardiac computed tomography" means the use of x-ray images taken from the patient at different angles to produce tomographic (cross-sectional) images.

Another means for imaging an arrhythmia includes echocardiography also known as "cardiac ultrasonoagraphy." As used herein, "cardiac ultrasonoagraphy" means the use of uses standard two-dimensional, three-dimensional, and/or Doppler ultrasound to create images of the heart.

"ECVUE" refers to an Electrocardiographic Mapping (ECM) platform that combines body surface electrical data with heart-torso anatomical data to provide simultaneous, multi-chamber 3D maps of the heart's electrical activity.

It is understood and herein contemplated that any of the above means for imaging an arrhythmia can be used in conjunction with one or more of the other means for imaging an arrhythmia as the data acquired can be complementary and nonduplicative. In one aspect, the of two or more sets of images can be aligned with each other (i.e., the images are co-registered). In some instances the use of one or more imaging means can be employed as a geometry determining device and one or more imaging means can be a device for measuring electrical potential. That is, the imaging can include electrophysiological signatures and/or anatomical signatures. Accordingly, in one aspect, disclosed herein are noninvasive systems for imaging and treating cardiac arrhythmia in a subject comprising a noninvasive means for imaging an arrhythmia and a noninvasive means for treating said arrhythmia, wherein the noninvasive imaging means comprises an electrical potential measuring device and a geometry determining device.

The electrical potential measuring device can comprise any mechanism for achieving such information including but not limited to an ECGI device or other like device comprising an electrode array of body surface electrodes. Thus, in one aspect, disclosed herein are noninvasive systems for imaging and treating cardiac arrhythmia in a subject comprising a noninvasive means for imaging an arrhythmia and a noninvasive means for treating said arrhythmia, wherein the noninvasive imaging means comprises an electrical potential measuring device and a geometry determining device, and wherein the electrical potential measuring device comprises an electrode array for measuring potentials at a plurality of locations on the subject. Such electrodes can be arranged in any manner conducive to accurately monitoring cardiac electrical potential including being a component of a wearable vest or strips that cover the subject's torso. It is understood that the electrical potential can be measured with at least 5, 10, 20, 25, 30, 40, 50, 60, 70, 80, 90, 100, 110, 120, 130, 140, 150, 160, 170, 180, 190, 200, 210, 220, 230, 240, 250, 260, 270, 280, 290, or 300 or more electrodes.

The geometry determining device can take a variety of forms including x-ray, ultrasonography, computed tomography (CT) and magnetic resonance imaging (MRI). For example, the geometry determining device can take the form of a CT scanner or MRI device. The operation and collection of data therefrom will be apparent to those of ordinary skill in the art. In this invention, the CT scanner/MRI device is used to generate data, or images, to determine torso geometry and, consequently, body surface electrode positions as well as an epicardial envelope surrounding the heart. As those of skill in the art will appreciate, the epicardial envelope is a suitable estimate of the epicardial surface itself, which can also be determined. It should also be recognized that locating the epicardial envelope or surface necessarily involves location of the heart. Preferably, if a CT scanner is used, the scanner will allow slice thickness between 1 mm and 8 mm and have adjustable kVp and mAs settings to perform a variety of different types of CT scans of different parts of the body. Moreover, the acquisition times can be on the order of 3 seconds or less.

Where the geometry device takes the form of a bi-plane x-ray machine, a three dimensional digitizer/locator can be used to obtain the torso geometry and the positions of body surface electrodes. The epicardial envelope is constructed from two bi-planar x-rays (30.degree. right anterior oblique, and 60.degree. left anterior oblique or other angles as required) using curve fitting techniques. Experiments have shown that two portable 3D digitizer systems (including two dedicated lap-top computers for data acquisition and storage) that are used together can digitize the entire torso in about 10 minutes. The preferred digitizers perform with 1 mm accuracy. Bi-planar x-rays are obtained with suitable x-ray equipment usually located in the catheterization laboratories.

In one aspect, it is understood that the mapping of the cardiac region can be realized with greater accuracy and efficiency through the use of an imaging processor (such as, a computer processor) configured to compute heart electrical activity data from a set of surface electrical potentials and determined geometries after which the processor generates an image of the heart (i.e., in one aspect, the processor interrogates either the electrophysiological signatures of arrhythmia, the anatomical signatures of arrhythmia, or both). This processor can be used to facilitate real-time acquisition of electrical potentials and determined geometries to provide the most current cardiac image.

It is understood and herein contemplated that the physician or other use utilizing the noninvasive system may desire to define the target based on the images generated by the imaging means. Thus, in one aspect, disclosed herein are noninvasive systems further comprises a peripheral for defining an arrhythmia target from the image generated by the imaging processor. It is understood and herein contemplated that the peripheral for defining an arrhythmia target can be a component of the imaging means or a component of the TPS. Thus, in one aspect, disclosed herein are noninvasive systems wherein the noninvasive imaging means further comprises a peripheral for defining an arrhythmia target from the image generated by the imaging processor. Also disclosed are; noninvasive systems comprising a TPS, wherein the TPS comprises a peripheral for defining an arrhythmia target from the image generated by the imaging processor.

Improvements in imaging and computer technology have led to advances in radiation treatment. The introduction of CT scanners enables surgeons and radiation oncologist to better define the location and shape of a target. Further improvements in imaging technology include MRI and PET scanners. In addition, radiation therapy has also been aided by enhancements in ancillary technologies such as simulators to help position patients and advanced computers to improve treatment planning to enable the radiation oncologist to deliver radiation from a number of different angles. Computer technology has been introduced that enable radiation oncologists to link CT scanners to radiation therapy, making treatment more precise and treatment planning faster and more accurate, thereby making more complex plans available. Such advancements allow integrated conformal therapy, in which the radiation beam conforms to an actual shape of a target to minimize collateral damage to the surrounding healthy tissue. By combining simulators and imaging and treatment planning computers, the irradiation can be precisely administered.

The electrophysiological and/or anatomical images generated by the noninvasive imaging means can be DICOM complaint which allows the images to be co-registered (i.e., aligned with other images) to the primary planning CT dataset as if they were any other secondary image (PET/CT, MRI, etc.) per standard treatment planning, and used as a method to define the arrhythmia target on the primary planning CT dataset. In one aspect, the processor (such as, a computer processor) for converting the images to be DICOM compliant can be a component of the noninvasive imaging means or as a component of the TPS. Disclosed herein are noninvasive systems comprising a noninvasive imaging means further comprising a processor (such as, a computer processor) configured for converting the defined target into a format that can be imported into a DICOM compliant treatment planning system. Also disclosed are noninvasive systems further comprising a processor (such as, a computer processor) for converting the defined target into a DICOM compatible format, wherein the processor is a component of the TPS. In one aspect, the processor for converting the defined target into DICOM complaint format further provides structure and dose data.

It is understood and herein contemplated that the disclosed systems can comprise a treatment planning system (TPS). As used herein, a "treatment planning system (TPS)" refers to processors specifically configured to plan noninvasive treatment (such as, for example, the treatments included herein, including but not limited to stereotactic body radiotherapy, stereotactic ablative radiotherapy, stereotactic radiosurgery, fractionated radiotherapy, hypofractionated radiotherapy, high-frequency/focused ultrasound, or lasers) through defining patient anatomy, tumor targets, and/or dose distributions. By using computerized planning and delivery, noninvasive therapy conforms the treatment (such as, for example, radiation) to the shape of a target. By using computers to analyze the treatment planning options, multiple beams of radiation match the shape of the target. The noninvasive system can then apply intense doses of high-energy radiation to destroy tissue in a single treatment or in multiple treatments. Accordingly, in one aspect, disclosed herein are noninvasive system for imaging and treating cardiac arrhythmia in a subject comprising a noninvasive means for imaging an arrhythmia, a treatment planning system, and a noninvasive means for treating said arrhythmia. In one aspect, the TPS is digital imaging and communications in medicine (DICOM) compliant.

By being DICOM compliant, the TPS can co-register the images generated with the noninvasive imaging system to the primary planning CT dataset as if they were any other secondary image (PET/CT, MRI, etc.) per standard treatment planning, and used as a method to define the arrhythmia target on the primary planning CT dataset. In one embodiment, the system comprises a processor configured to allows the user to define the arrhythmia target using ECGI data, overlay that target as a coloring of the CT image set, and parse the CT data back into axial CT slices that can be imported into any DICOM compliant treatment planning system (TPS). These images can be subsequently co-registered to the primary planning CT dataset per standard treatment planning, and used as a method to define the arrhythmia target on the primary planning CT dataset. Thus, in one aspect, the TPS comprises a processor for importing DICOM compliant images and target information into the treatment planning system.

In another embodiment, the system comprises a processor configured to allows the user to define the arrhythmia target using ECGI data, reconstruct that target as a DICOM-RT compliant structure registered to the ECGI CT, and then exported as a DICOM-RT structure set with reference CT. These DICOM-RT compliant files can then be imported into any DICOM compliant treatment planning system (TPS). These images can be subsequently co-registered to the primary planning CT dataset and the target as defined by the dose cloud used to define a target in the TPS and/or defined in the structure set re-mapped or transferred to the primary planning CT dataset using standard tools available in all TPS.

In one aspect, the processor can be so configures to allow the user to define the arrhythmia target using ECGI data in real-time while the patient is on the treatment machine, and direct therapy to the target using the ECGI data.

The disclosed systems utilize noninvasive therapies for treating an arrhythmia. Such noninvasive methods can include, but are not limited to stereotactic body radiotherapy, stereotactic ablative radiotherapy, stereotactic radiosurgery, fractionated radiotherapy, hypofractionated radiotherapy, high-frequency/focused ultrasound, or lasers. Stereotactic body radiotherapy (SBRT), also known as stereotactic ablative radiotherapy (SABR) or stereotactic radiosurgery (SRS), is a culmination of several decades worth of progress in radiation oncology, allowing for the precise delivery of high doses of radiation to targets in the body over few (typically, <5) fractions with minimal exposure of normal adjacent tissue.

Radiation can be administered with either x-rays/photons (typically with a linear accelerator), γ-rays (such as with a Co-60 unit), or charged particles (protons, carbon, helium, etc.). A variety of delivery systems exist, all of which have various delivery methods. However, all radiotherapy delivery hinges on the fundamental tenets of optimizing immobilization, assessment and accounting of motion in treatment planning and delivery, the ability to create and deliver compact precise dose distributions to maximize dose to the target while minimizing dose to healthy tissues, and image-guidance.

In one aspect the noninvasive systems disclosed herein, further comprising a source of radiation operatively linked to a radiotherapy delivery unit comprising a controller and a processor for coordinating the precise delivery of radiation to a target area as informed by an image or images (e.g., electrophysiological signatures and/or anatomical signatures) of the target area generated by the imaging processor. In one aspect, the controller that is operatively linked to a source of radiation can be, for example, a robotic controller and a processor for coordinating the precise delivery of radiation to a target area can control the movement of the robotic arm. Such a radiotherapy system can include a radiotherapy delivery unit whose radiation beam can be shaped and directed to a target and/or a lightweight linear accelerator mounted to a highly maneuverable robotic arm. An image guidance system can use image registration techniques to determine the target site coordinates with respect to the radiotherapy delivery unit's radiation beam as determined from the imaging means, and transmits the target coordinates to a controller (for example, a controller as a component of a radiotherapy delivery unit or a robotic arm) which then directs the radiation beam to the treatment site. In one aspect, the system can be automated in real time such that when the target moves, the system detects the change and corrects the beam pointing in near real-time. Near real-time image guidance can avoid any need for skeletal fixation to rigidly immobilize the target. It is understood and herein contemplated that a radiotherapy delivery unit can comprise systems that are C-shape, O-shape, protons, combination of a CT and a linac, MIR and a linac, PET scanner and a linac, CT and protons, MR and protons, PET and protons, or any rational combination of imaging and treatment delivery system.

In the exemplary embodiment, radiation therapy is delivered using on a Varian TrueBeam, a C-shaped, image-guided radiotherapy (IGRT)-equipped linear accelerator. These units are equipped with an onboard cone beam CT (CBCT) which allows for acquisition of high fidelity volumetric images of the thorax which can be directly registered to the medical images used in the treatment planning system, allowing for accurate, near real-time alignment of the heart and target volume. A high-definition multi leaf collimator (or MLC) is what shapes the beam. It has 120 computer-controlled "leaves" or "fingers" that create apertures of different shapes and sizes. The leaves sculpt the beam to match the 3-D shape of the defined target area. These can move and change during treatment better deliver the radiation to the target while minimizing the dose to the surrounding healthy tissue. Real-time imaging tools allow clinicians to "see" the target they are about to treat. This allows them to hit the target with accuracy measured in millimeters. The system includes a new "gated" option for synchronizing beam delivery with breathing. This helps maintain accuracy as the system changes its targeting whenever tumor motion is an issue, for example during lung cancer treatments. Use of this system precludes the need for invasive placement of a fiducial marker.

In another embodiment, the radiation is delivered from a lightweight linear accelerator attached to a robotic arm that is part of a pure robotics system, providing six degree of freedom range of motion. In use, the surgeon physician basically pushes a button and the non-invasive procedure is performed automatically with the image guidance system continuously checking and re-checking the position of the target tissue and the precision with which linear accelerator is firing radiation at the target. An image guidance system provides image guidance (such as, x-ray, ultrasonography, MRI, or CT guidance) that gives the surgeon the position of internal organs and skeletal anatomy. Image guidance continuously checks, during a procedure, that the target is at the same place at the end of the treatment that it was at the beginning. The exemplary image guidance system included with the Accuray CyberKnife™ radiosurgery system takes the surgeon's hand out of the loop. The surgeon may not even be in the operating room with the patient. Instead, the image guidance system guides the procedure automatically on a real-time basis.

Radiosurgery uses precise spatial localization and large numbers of cross-fired radiation beams. Because of the high dosage of radiation that can be administered, such radiosurgery is generally more precise than other radiation treatments, with targeting accuracies of 1 to 2 mm. Preclinical data and early clinical data have examined a wide range of radiation doses (17.5 to 50 Gy in a single fraction) and target volumes (1 to >100 cc). Thus, the radiation dose can used in the disclosed methods and systems be any amount of radiation between about 15 Gy and 75 Gy. Preferably, the radiation dose is between 15 Gy and 50 Gy. For example, the dose can be between about 15 Gy to about 50 Gy, from 17.5 Gy to about 50 Gy, from about 17.5 Gy to about 40 Gy, from about 20 Gy to about 30 Gy, or from about 20 Gy to about 25 Gy. In one aspect, the radiation dose can be 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 35, 36, 37, 38, 39, 40, 41, 42, 43, 44, 45, 46, 47, 48, 49, 50, 55, 60, 65, 70, 75 Gy or any amount of radiation in between. Similarly, the target volume used in the methods and systems disclosed herein can be any dose volume between about 1 cc to about 100 cc, preferably between about 40 cc and about 55 cc. Thus, the target volume can be between about 1 cc to 100 cc, between about 15 cc to about 85 cc, between about 17 cc to about 81 cc between about 20 cc to about 75 cc, between about 30 cc to about 65 cc, or between about 40 cc to about 55 cc. In one aspect, the target volume can be 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.3, 17.5, 18, 18.5, 19, 19.5, 20, 21, 22, 23, 24, 25, 26, 27, 28, 29, 30, 31, 32, 33, 34, 35, 36, 37, 38, 39, 40, 41, 42, 43, 44, 44.5, 45, 46, 47, 48, 49, 50, 51, 51.3, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 81.1, 82, 83, 84, 85, 86, 87, 88, 89, 90, 91, 92, 93, 94, 95, 96, 97, 98, 99, or 100 cc, or any volume in between. It is understood that the noninvasive treatment could be applied to any combination of this wide range of doses and target volumes, and is not in and of itself limited to delivery of doses and volumes outside this range if they are deemed to be clinically indicated. For example, the radiation dosage can be 25 Gy and the target volume 44.5 cc. Other examples of combinations of dosage and target volumes include, but are not limited to 25 Gy and 17.1 cc, 25 Gy and 51.3 cc, 25 Gy and 44.5 cc, 25 Gy and 45 cc, 25 Gy and 46 cc, 25 Gy and 47 cc, 25 Gy and 48 cc, 25 Gy and 49 cc, 25 Gy and 50 cc, 25 Gy and 51 cc, 25 Gy and 52 cc, 25 Gy and 53 cc, 25 Gy and 81.1 cc, 20 Gy and 44 cc, 20 Gy and 45 cc, 20 Gy and 46 cc, 20 Gy and 47 cc, 20 Gy and 48 cc, 20 Gy and 49 cc, 20 Gy and 50 cc, 20 Gy and 51 cc, 20 Gy and 52 cc, 20 Gy and 53 cc, 20 Gy and 54 cc, 20 Gy and 55 cc, 30 Gy and 44 cc, 30 Gy and 45 cc, 30 Gy and 46 cc, 30 Gy and 47 cc, 30 Gy and 48 cc, 30 Gy and 49 cc, 30 Gy and 50 cc, 30 Gy and 51 cc, 30 Gy and 52 cc, 30 Gy and 53 cc, 30 Gy and 54 cc, 30 Gy and 55 cc, 40 Gy and 44 cc, 40 Gy and 45 cc, 40 Gy and 46 cc, 40 Gy and 47 cc, 40 Gy and 48 cc, 40 Gy and 49 cc, 40 Gy and 50 cc, 40 Gy and 51 cc, 40 Gy and 52 cc, 40 Gy and 53 cc, 40 Gy and 54 cc, 40 Gy and 55 cc, 50 Gy and 44 cc, 50 Gy and 45 cc, 50 Gy and 46 cc, 50 Gy and 47 cc, 50 Gy and 48 cc, 50 Gy and 49 cc, 50 Gy and 50 cc, 50 Gy and 51 cc, 50 Gy and 52 cc, 50 Gy and 53 cc, 50 Gy and 54 cc, and 50 Gy and 55 cc.

It is further contemplated herein that multiple administrations of radiation may be needed to achieve a desired dose or to achieve the therapeutic goal where multiple doses of radiation are prescribed. Disclosed herein are systems and methods where radiation is administered 1, 2, 3, 4, 5, 6, 7, 8, 9, or 10 times in order to achieve a desired radiation dose, and/or system where a desired dose of radiation is administered 1, 2, 3, 4, 5, 6, 7, 8, 9, or 10 times.

It is understood and herein contemplated, that the disclosed system (as exemplified by FIGS. 1A and 1B) can be used to facilitate treatment of a cardiac arrhythmia. Thus, in one aspect, disclosed herein are noninvasive methods of treating cardiac arrhythmia comprising computing heart electrical activity data corresponding to heart electrical activity from a set of noninvasively measured body surface electrical potentials, generating a display based on the heart electrical activity data; determining one or more target treatment regions; directing a noninvasive therapy to the one or more target regions.

The imaging and/or treatment methods disclosed herein can comprise any aspect or combination of the noninvasive imaging and/or treatment system disclosed herein. In one aspect, the computation of heart electrical activity data corresponding to heart electrical activity can be obtained from any one or more of the imaging devices disclosed herein including, but not limited to, electrocadiagraphic imaging (ECCI), magnetic resonance imaging, cardiac computed tomography, cardiac nuclear medicine, cardiac ultrasonoagraphy, ECVUE, or x-ray. It is understood and herein contemplated that the use of one or more of the disclosed imaging devices can generate an epicardial or endocardial cardiac surface potential map as well as anatomical maps. Thus, in one aspect, disclosed herein are methods of treating an arrhythmia comprising generating a display based on the heart electrical activity data, wherein the display generated is a cardiac surface potential map.

In one aspect, the disclosed treatment methods can utilize the TPS as disclosed herein.

It is understood that the noninvasive treatment can utilize any of the therapeutic devices disclosed herein to treat the target. In one aspect, disclosed herein are noninvasive methods of treating an arrhythmia, wherein the noninvasive therapy comprises stereotactic body radiotherapy, stereotactic ablative radiotherapy, stereotactic radiosurgery, fractionated radiotherapy, hypofractionated radiotherapy, high-frequency/focused ultrasound, or lasers As disclosed herein, the electrical activity obtained can be achieved in real-time and combined with real-time geometry determinations to produce a real-time image of the heart and treatment target. In one aspect, this real-time imaging can facilitate the ability to adjust targeting in real-time as well. In one aspect, disclosed herein are methods of treatment, further comprising adjusting the targeting of the noninvasive therapy to reflect real-time electrical activity data.

In one aspect, it is understood that the disclosed methods can comprise the use of specifically configured processors to produce an image and provide targeting input to a treatment delivery device (for example, a delivery unit, including, but not limited to systems that are C-shape, O-shape, protons, combination of a CT and a linac, MR and a linac, PET scanner and a linac, CT and protons, MR and protons, PET and protons, a robotic delivery unity, or any rational combination of imaging and treatment delivery system) and control the movement of said device and the administration of the therapy can provide the greatest degree of control over the therapy and any real-time adjustments to the therapy. In one aspect, disclosed herein are methods of treating arrhythmia, wherein the imaging and therapy delivery are part of an integrated system including the delivery of the therapy.

It is understood and herein contemplated that the noninvasive therapy used in the noninvasive methods disclosed herein can be a radiotherapy and can comprise any dosage, volume, or frequency disclosed above for use in the noninvasive systems disclosed herein.

In one aspect, it is understood that the disclosed methods can comprise the use of specifically configured processors to allow the user to define the arrhythmia target using ECGI data overlaid on a CT image set of a patient's torso and then translate the defined target on the CT image set back into axial CT slices that can be imported into any DICOM compliant treatment planning system (TPS). These images can subsequently be co-registered to the primary planning CT dataset per standard treatment planning, and used to define the arrhythmia target on the primary planning CT dataset.

In one aspect, it is understood that the disclosed methods can comprise the use of specifically configured processors to allow the user to define the arrhythmia target using ECGI data, reconstruct that target as a DICOM-RT compliant structure registered to the ECGI CT, and then exported as a DICOM-RT structure set with reference CT. These DICOM-RT compliant files can then be imported into any DICOM compliant treatment planning system (TPS). These images can be subsequently co-registered to the primary planning CT dataset and the target as defined in the structure set re-mapped or transferred to the primary planning CT dataset using standard tools available in all TPS.

In one aspect, it is understood that the disclosed methods can comprise the use of specifically configured processors to allow the user to define the arrhythmia target using ECGI data, reconstruct that target as a DICOM-RT compliant dose object registered to the ECGI CT, and then exported as a DICOM-RT dose with reference CT. These DICOM-RT compliant files can then be imported into any DICOM compliant treatment planning system (TPS). These images can be subsequently co-registered to the primary planning CT dataset and the target as defined by the dose cloud used to define a target in the TPS.

In one aspect, it is understood that the disclosed methods can comprise the use of specifically configured processors to allow the user to define the arrhythmia target using ECGI data in real-time while the patient is on the machine, and direct therapy to the target using the ECGI data.

B. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations can be accounted for. Unless indicated otherwise, parts are parts by weight, temperature is in ° C. or is at ambient temperature, and pressure is at or near atmospheric.

Example 1

EP-Guided Noninvasive Cardiac Radioablation (ENCORE) for Ventricular Tachycardia (VT)

Parallel advances have enabled noninvasively mapping cardiac arrhythmias using electrocardiographic imaging (ECGI) and delivering precise ablative radiation with stereotactic body radiation therapy (SBRT). This report details the first use of catheter-free, Electrophysiology (EP)-guided Noninvasive Cardiac Radioablation (ENCORE) for ventricular tachycardia (VT).

a) Results (1) Patients

From April 2015 through November 2015, nine patients were screened for the procedure; five received the treatment. Of the four patients who did not receive treatment, two declined participation (one chose hospice and died from VT complications one week later, one chose another invasive VT ablation procedure), one patient agreed to treatment but died of progressive cardiogenic shock following SBRT simulation but prior to treatment, and one patient underwent implantation of a left ventricular assist device, with recurrent severe VT storm immediately after surgery. Table 1 summarizes our experience to date.

TABLE 1

Summary of Wash U ENCORE clinical experience to date.

| Pt | Age (years) | Sex | Prior catheter ablations | Target | Target volume (ITV, cc's) | Dose (Gy) in 1 fx | Follow-up as of May 23, 2016 | Delivery | Number of VT episodes in 3 months before ENCORE | Number of VT episodes after ENCORE | Other |
|---|---|---|---|---|---|---|---|---|---|---|---|
| 1 | 61 | M | 1 | Anteroseptal to anterolateral LV base | 51.3 | 25 | 13 mo | 2 arc VMAT | >30 | 1 at 12 months, now off meds | No toxicity |
| 2 | 60 | M | 0 (contraindicated due to recent heart surgery) | Focal anterolateral LV base | 17.3 | 25 | 10 mo | Non-coplanar IMRT | >17 | 3 in first week, now off meds | No toxicity |
| 3 | 65 | M | 2 | Inferior LV | 44.5 | 25 | 10 mo | 2 arc VMAT | 5 | 1 at 6 months, now off meds | No toxicity. |
| 4 | 62 | M | 6 | Septal RVOT, LV summit, LV basal septum | 53.0 | 25 | 7 mo | 2 arc VMAT | >1000 | Invasively mapped 4 weeks post treatment. 0 since, off meds | No toxicity. |
| 5 | 83 | F | 0 (contraindicated due to severe comorbidities) | Mid inferior, inferolateral LV | 81.1 | 25 | 2 weeks (censored) | 3 arc VMAT | >1000 | 233 VT episodes over 13 days after treatment | Embolic stroke 13 days after ENCOREtx. Unclear relationship. |

Mean age of the five patients who received treatment was 66 years (range 60-83 years). All had significant VT burden despite multiple medical and invasive therapies. The mean number of cardiac defibrillator (ICD)-treated VT episodes three months before treatment was 1315 (range 5 to 4312 VT episodes). All patients were on two antiarrhythmic drugs at the time of evaluation. Three patients had failed prior invasive catheter ablation procedures (mean 2 procedures, range 1-4). Two patients had contraindications to invasive catheter ablation: one with a new mechanical prosthetic mitral valve and evidence for epicardial VT; one deemed too frail for any invasive procedures but refused hospice care. All five had severe heart failure symptoms, with four of the five in NYHA class 4 heart failure. Mean left ventricular ejection fraction (LVEF) was 23% (range 15-37%). Of the first 3 patients, all had a dramatic reduction in the number and frequency of VT episodes after ENCORE, and all eventually had termination of VT. The 2 most recent patients had substantially more VT (both over 1000 episodes in the month before), and one of the two patients was demonstrating a reduction in VT pattern as of censored follow up. Only one of the five patients who received ENCORE protocol did not have an improvement in VT burden.

(2) ENCORE Procedure

All patients underwent ECGI noninvasive mapping: four patients had inducible VT (mean 3 VTs, range 1-5 induced VTs). ECGI was performed for all induced VTs. For all 12 distinct induced VTs, the site of earliest ventricular activation (site of origin) was adjacent to myocardial scar. FIG. 4 is an example of an ENCORE treatment plan for patient #1., targeting an area of anatomic scar that was identified with DE cMRI which overlapped with the area of electrical abnormalities based on 12-lead ECGs of VT obtained during noninvasive programmed stimulation procedure (NIPS). In all cases, overall treatment time is substantially faster than the previously reported cases in the literature, which results in improved patient comfort and may also improve overall delivery accuracy, as increased time on the treatment machine has been correlated with "drift" away from the isocenter over time.

Treatment characteristics are reported in Table 2. Ablation target volumes ranged from 17 to 81 cc (mean 49 cc). On-table treatment times ranged from 11 to 18 minutes (mean 14 minutes), performed awake. No patients reported any acute symptoms during treatment.

TABLE 2

Treatment Characteristics

| Treatment Characteristics | Value | Range |
|---|---|---|
| Number of induced VT during NIPS | 3 induced VT (mean) | 0-5 induced VT |
| Ablation target volume | 49 cc (mean) | 17-81 cc |
| Treatment time | 15 mins (mean) | 11-18 mins |
| Length of hospital stay after treatment | 2 days (mean) | 1-3 days |

(3) Ventricular Tachycardia Burden

Significant reduction in VT burden and ICD therapies was achieved in all patients after treatment (FIG. 2). This effect is seen in the absence of antiarrhythmic medications, which were aggressively weaned off in the first 6 weeks after treatment. FIG. 2A shows the monthly number of ICD therapies on per-patient basis. After the 6-week blanking period, VT was exceedingly rare: 4 VT events occurred in 49 patient-months (median 12 month follow up). Per patient, comparing three months before the treatment to twelve months after treatment, there was a strongly significant reduction in VT burden (mean 1315 VT episodes vs. 1 VT episodes, p<0.001). The improvement was observed for both ICD shocks (FIG. 2B) and ICD anti-tachycardia pacing episodes (FIG. 2C).

(4) Adverse Events

Figure 2A:
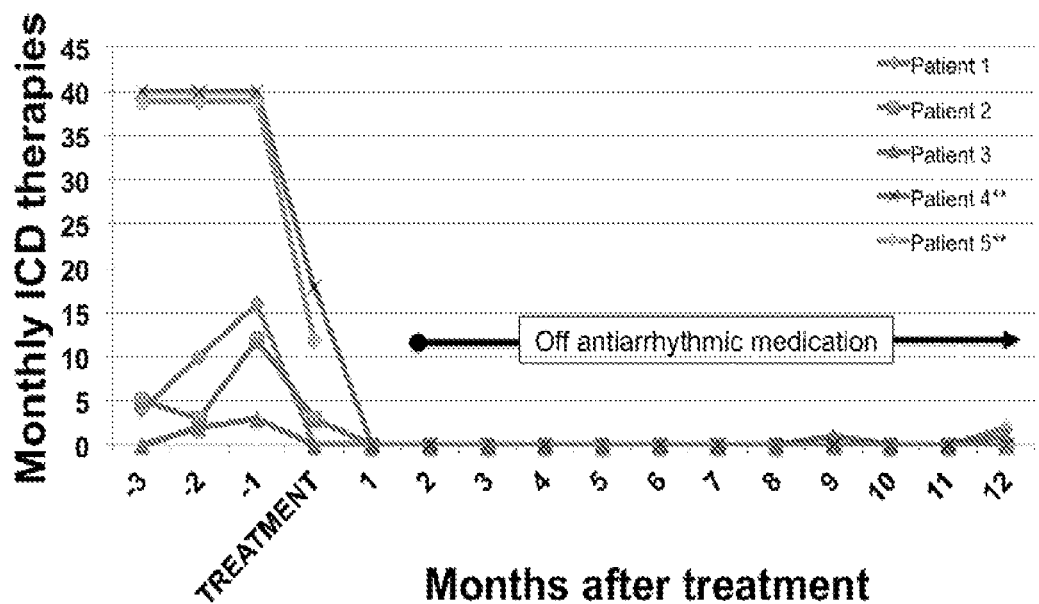
FIG. 2A shows the monthly number of ICD therapies on per-patient basis.
Figure 2B:
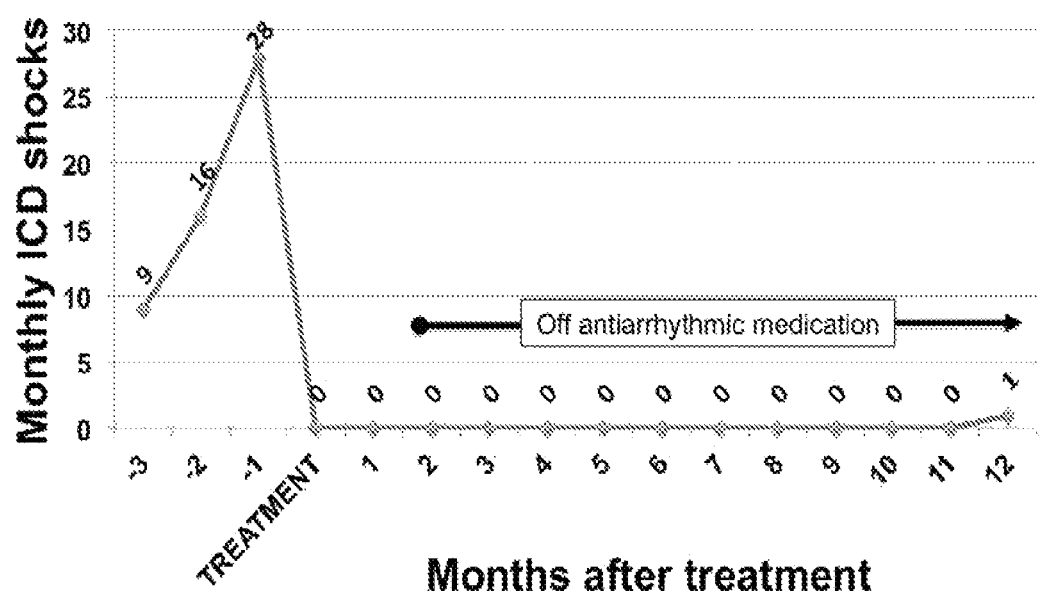
FIG. 2B shows monthly number of ICD shocks and the improvement that was observed for ICD shocks.
Figure 2C:
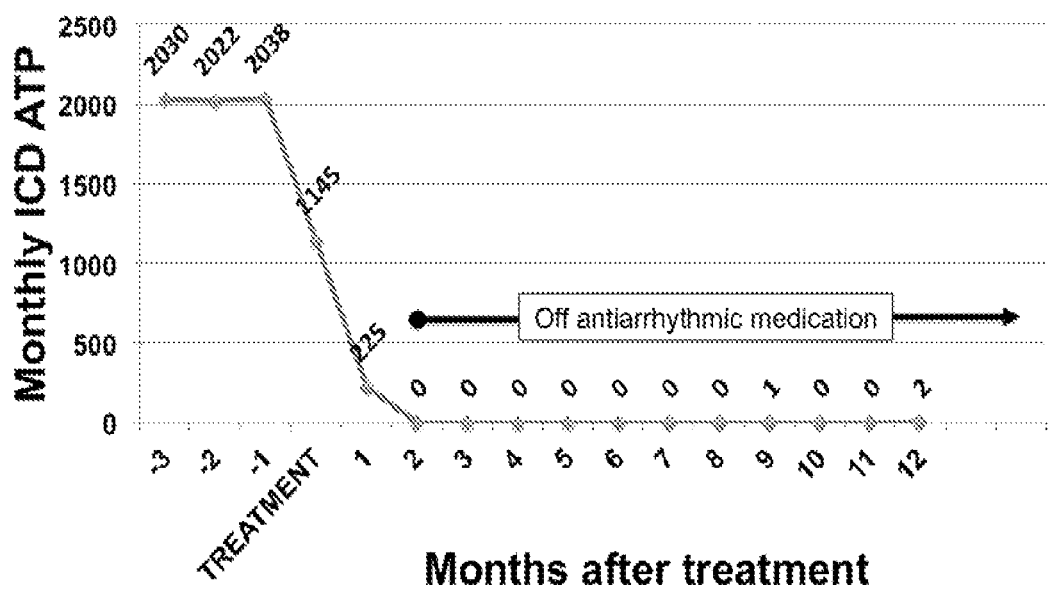
FIG. 2C shows the cumulative number of monthly ICD Anti-Tachycardia Pacing. Improvement was observed for ICD anti-tachycardia pacing episodes.
Figure 2D:
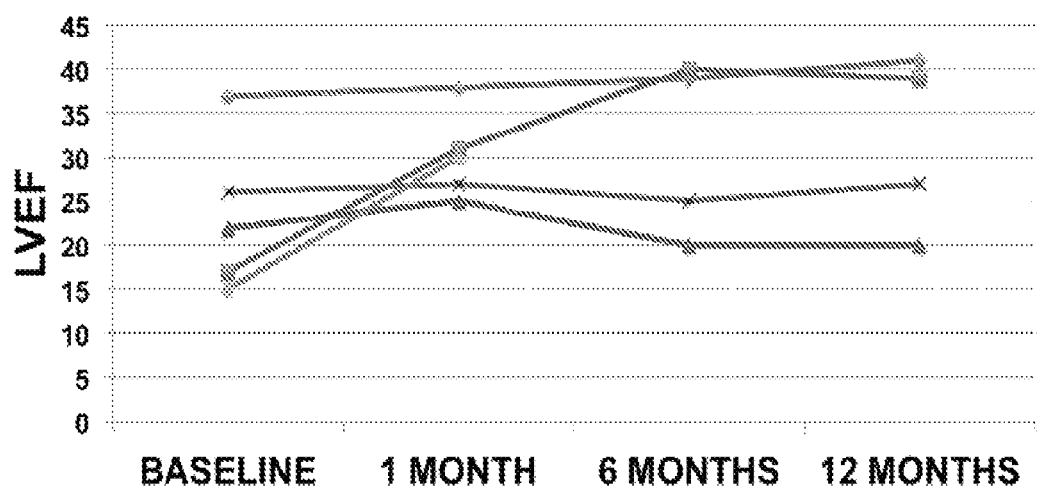
FIG. 2D shows that the left ventricular ejection fraction remained stable or improved for all patients in both short- and long-term follow-up.
Figure 2E:
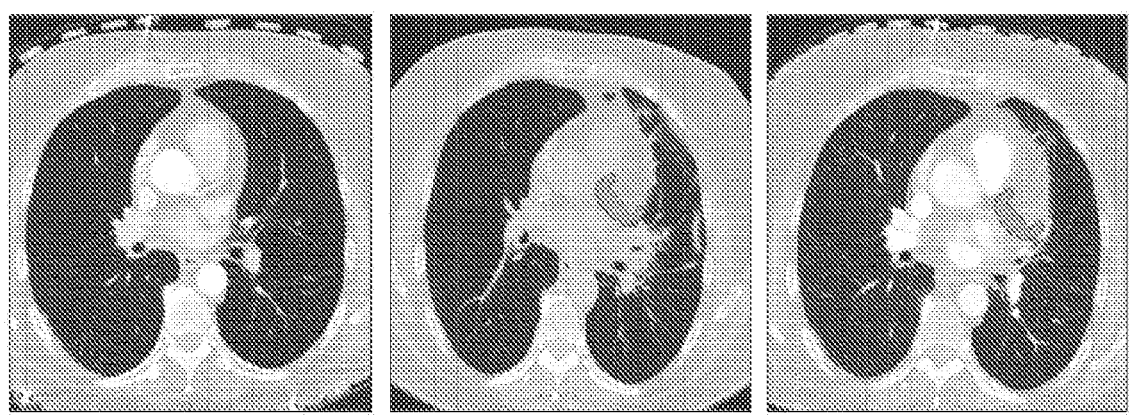
FIG. 2E shows serial CT scans at baseline, 3 months post treatment and 12 months post treatment.

No treatment-related complications occurred during the treatment or during the index hospitalization. No acute changes were seen on ICD interrogation after treatment. Patients were discharged home 1-3 days after treatment. Three patients described fatigue in the day after treatment; none described chest pain or discomfort. No heart failure exacerbations occurred in the immediate timeframe after treatment. Serial cardiac echocardiography demonstrated no pericardial effusions and no negative changes in wall motion at the specific location of therapy for any patient. The longitudinal heart function, as measured by cardiac echocardiography, is shown in FIG. 2D. None of the 5 patients had a reduction in LVEF after treatment (mean +5% in LVEF, range 0 to +15%). In other words, overall left ventricular ejection fraction remained stable or improved for all patients in both short- and long-term follow-up (FIG. 2D). No clinical pulmonary symptoms nor complications occurred after treatment. Serial CT scans at 3 months demonstrated mild adjacent lung inflammatory changes typical of thoracic SBRT, which largely resolved at one year (FIG. 2E).

During follow up, after stopping antiarrhythmic medications, sinus node function recovered in three patients and occasionally exceeded the programmed rate cut off of the ICD detection for VT (100 bpm) resulting in one inappropriate ATP. ICD reprogramming was required.

One patient (Patient 5) suffered a stroke 3 weeks after treatment. This 83 year-old female patient had a history of atrial fibrillation and other risk factors for a stroke, but was deemed too frail to take oral anticoagulants. Her VT burden was reduced by 72% in the 3 weeks after the noninvasive ablation, and her LVEF had improved from 15% to 30%. No intracardiac thrombus was seen on cardiac echocardiography, or after pathologic assessment (see below). Her stroke was deemed likely to be related to known previous conditions rather than the noninvasive ablation treatment.

(5) Cardiac Radiobiological Effect

Patient 5 generously provided her heart for pathological assessment after her death. On histologic examination, the most distinct finding related to radiation exposure was the presence of prominent ectatic vessels, primarily of small arterioles and venules (FIG. 3). This unusual vascular pattern was largely located at the interface of the prior infarction and viable myocardium. This ectatic pattern has been previously described as a component of acute vascular injury, usually seen in the early weeks following radiation exposure accompanied by endothelial cell swelling, vacuolization, and perivascular tissue edema. However, in this case, the endothelial lining of these vessels appeared normal and non-reactive, without evidence of an acute vasculitis or tissue edema. No evidence of myocyte necrosis, hemorrhage, or acute inflammation related to the treatment was observed.

b) METHODS (1) Patients

Patients with severe, symptomatic, treatment-refractory ventricular tachycardia with limited or absent reasonable conventional therapeutic options were considered for cardiac radioablation. In general, patients were considered if they had at least 3 episodes of ICD-treated VT in the preceding 3 months, despite use of at least two antiarrhythmic medications and at least one catheter ablation procedure. Patients with a contraindication to catheter ablation were also considered. All patients were inpatients, with ongoing regular VT episodes despite aggressive IV and oral antiarrhythmic therapies. Cardiac transplant evaluation was encouraged, but transplant eligibility was not an absolute condition for consideration.

(2) Procedural Workflow

Prior to treatment, patients underwent noninvasive ECGI during induced VT to precisely identify the critical electrical elements of VT. Patients wore a vest of 256 electrodes (BioSemi, Netherlands) with small radiopaque markers attached at the location of the electrodes to visualize on cardiac imaging. A chest CT was obtained to provide patient-specific heart-torso geometry and location of the body surface electrodes. After the CT scan, patients were brought to the EP laboratory, provided light sedation, and prepped for a noninvasive-programmed stimulation (NIPS) procedure. The patient's ICD was used to pace the heart using a standard protocol with the intent of inducing VT. Once sustained VT was induced, a 12-lead ECG and 256-lead body surface electrical map was obtained for use with ECGI. The ICD was then used to terminate the VT with a brief overdrive pacing maneuver.

Information from the CT scan and the body surface mapping during VT was combined in methods described previously (3-6) By "solving" the inverse solution, the electrical information was transferred from the body surface to the epicardial surface of the patient's heart 3D reconstruction. This allowed for exact noninvasive identification of the earliest electrical activation in VT, which was considered to be the site of origin, exiting the ventricular scar.

In addition to cardiac electrical maps generated from ECGI, patients also underwent anatomic imaging to identify regions of scar with either resting single-photon emission computed tomography (SPECT) or contrast-enhanced cardiac myocardial resonance imaging (MRI). The electrical information from ECGI and the anatomic scar information were combined to build a volumetric target for radioablation, targeting the location of the first 10 ms of VT and the full myocardial thickness of the associated ventricular scar.

(3) Targeting

Prior to treatment, patients underwent noninvasive ECGI during induced VT to precisely identify the critical electrical elements of VT. For ECGI, patients wore a vest of 256 electrodes (BioSemi, Netherlands) and underwent chest CT. Patients were brought to the EP laboratory and underwent noninvasive-programmed stimulation (NIPS) procedure using indwelling ICD to induce VT. Data for ECGI maps were instantly obtained, and the ICD was used to terminate VT with a brief overdrive-pacing maneuver. ECGI maps were created to identify the earliest electrical activation in VT.

Patients underwent additional imaging to identify regions of anatomic scar with either resting single-photon emission computed tomography (SPECT) or contrast-enhanced cardiac myocardial resonance imaging (MRI). Electrical information from ECGI and anatomic scar information were combined to build a volumetric target for radioablation, targeting the first 10 ms of VT and the full myocardial thickness of the associated ventricular scar.

(4) Delivery

Several days prior to treatment, patients underwent simulation, which included immobilization using a vacuum-assisted device (BodyFIX, Elekta, Stockholm, Sweden) and acquisition of a respiratory correlated CT (4D-CT) to assess the sum total of cardiac and pulmonary motion. The ablation target volume was contoured on the simulation CT. Additional expansion of this volume (internal target volume, ITV) was made using a maximum-intensity projection (MIP) of 4D-CT data to account for motion. Notably, in all patients the portion of the heart being targeted was largely akinetic due to preexisting cardiac disease. A final planning target volume (PTV) was created by volumetric expansion of the ITV by 5 mm in all directions to account for any residual uncertainties in patient setup, motion, and delivery.

A total dose of 25 Gy in a single fraction was prescribed to the PTV with a goal of achieving maximal coverage of PTV while avoiding dose in excess of calculated dose constraints to surrounding organs at risk such as the esophagus, stomach, lungs, and spinal cord. All plans were subjected to, and passed, standard internal physics quality insurance on a calibrated phantom prior to delivery.

Stereotactic radioablation was performed using an image-guided radiotherapy-equipped linear accelerator (TrueBeam, Varian Medical Systems, Palo Alto) which uses a cone beam CT (CBCT) to acquire images of the thorax which can be directly registered to the planning CT. This results in accurate, near real time alignment of the heart and target volume without need for invasive placement of a fiducial marker. For treatment, patients were placed in their custom immobilization device, aligned using the CBCT with verification of this alignment using fluoroscopy, and treated without use of any additional intrafraction imaging.

(5) Outcome Assessments (a) Visits

After treatment, patients were followed daily in the hospital on continuous cardiac monitoring. Prior to discharge, cardiac defibrillators (ICDs) were reprogrammed with a VT monitor-only zone at 100 bpm to assess for any possible VT during follow up. Follow up visits were per standard clinical practice. In brief, all patients were enrolled in a device remote monitoring program to enhance rapid interpretation of any ICD therapy. Patients were seen in outpatient clinic with ICD interrogations every two weeks for two months, monthly for the next four months, then again one year after treatment. At each follow up visit, if no further ventricular arrhythmias were detected, doses of antiarrhythmic medications were reduced or stopped entirely, with the goal of being off antiarrhythmic medication at the 6-week follow up visit.

(b) Efficacy

At each visit, patients' cardiac defibrillators (ICDs) were interrogated to assess for ventricular arrhythmias. ICD therapies were tallied as a sum total of ICD shocks and ICD anti-tachycardia pacing for ventricular arrhythmias. The treating electrophysiologist adjudicated all stored events.

(c) Safety

Adverse events were categorized as being specifically associated with stereotactic radioablation, medication regimen, or related to underlying conditions such as advanced heart failure or other arrhythmias. At every visit, both a cardiac electrophysiologist and a radiation oncologist evaluated patients. Patients underwent echocardiograms at baseline, 1 month, 6 months and 12 months after treatment to assess for cardiac adverse events. Patients also underwent chest CT scans at baseline, 3 months and 12 months to assess for thoracic adverse events.

c) Discussion

In this detailed descriptive analysis of five patients with treatment-refractory ventricular tachycardia, durable reduction in VT burden was achieved using an entirely noninvasive method for mapping and treating the arrhythmogenic area of the heart. These findings are even more striking in that: 1) patients were end-stage, with very low chances of VT-free survival; 2) patients were safely able to stop antiarrhythmic medications shortly after treatment; 3) treatment times were under 20 minutes.

Worldwide, invasive catheter ablation is increasingly performed to treat VT. The procedure is particularly effective in the absence of ventricular scar (idiopathic VT), where the trigger for arrhythmia can be focally ablated with radiofrequency energy. Catheter ablation for cardiomyopathic VT is more challenging and is associated with less favorable outcomes. VT recurrence rates can be as high as 50-70%. These procedures target large elements of abnormal ventricular scar that harbor critical components of the VT circuit. Because of the larger distribution of abnormal myocardium, VT recurrences are more common, especially in cases of extensive scar distribution (whereby many possible VT circuits exist) and scar that is distributed throughout the depth of the myocardium, outside the reach of standard radiofrequency ablation catheters. Recently published data point to improved success rates with more extensive ablation and with use of a combined endocardial and epicardial approach to ablate from both directions in an effort to "homogenize" the scar.

Because of the detailed nature of invasive point-by-point mapping, invasive scar-based VT ablation procedures require several hours. This long exposure to general anesthesia can be risky for patients with advanced cardiomyopathy, leading to prolonged hypotension, increased use of external hemodynamic support and ultimately lower rates of survival.

Stereotactic radioablation is well suited to achieve the full-thickness, gap-free homogenizing ablation that has been associated with better outcomes. In published pre-clinical data, the mature radioablation lesion extends from endocardium to epicardium, without gaps. This introduces a new concept of "volumetric ablation" to clinical electrophysiology. The sustained antiarrhythmic effect observed out to one year in the ENCORE-treated patients is due to a complete, distributed ablation volume of radiotherapy that treats the VT circuits that exist within the scar presently, as well as future, inchoate VT circuits. Published clinical data for anatomic-based, minimally invasive cardiac SBRT using a similar "volumetric ablation" approach has shown promising clinical results in two patients with refractory VT, similar to those in the cohort.

A significant advantage to the ENCORE procedure is the short duration of the treatment (14 minutes on average) performed while awake, eliminating the risks of general anesthesia and prolonged procedures. However, compared with the thermal injury of invasive radiofrequency ablation, an important theoretical disadvantage of radiotherapy is the lack of an immediate effect. In all five patients, a measurable antiarrhythmic effect was seen within the first days to weeks. Further pre-clinical studies are warranted to describe the time course of the anti-arrhythmic effect of radiotherapy as well as the biologic mechanisms driving this early effect.

Patients with end-stage VT refractory to medications and standard catheter ablation techniques have a very poor prognosis due to progressive heart failure and irrepressible VT (26). Recurrent VT after ablation is associated with 4- to 6-fold higher odds of death. Most patients who die within 6 months of an ablation procedure had a failed ablation and recurrent VT. More invasive methods for refractory VT include transcoronary ethanol ablation and surgical approaches to the epicardium. With increasingly aggressive invasive procedures, ICD shocks were significantly reduced (median 8 shocks per month to 1), but overall complication rates were high (25%). Only 33% remained VT-free at one year on 2 antiarrhythmic medications, and only one patient out of 67 was VT-free, off medication. This protocol represent an important treatment in the limited armamentarium to achieve arrhythmia control in patients with refractory VT.

What is claimed is:

1. A noninvasive system for imaging, planning, and treating cardiac arrhythmia in a subject, the system comprising:
    a noninvasive means for imaging a heart of the subject and identifying an arrhythmia comprising:
        an array of body surface electrodes for noninvasively measuring electrical potentials at a plurality of locations on the subject to identify the arrhythmia, and
        a geometry determining device for noninvasively obtaining a heart-torso geometry of the subject comprising an image data type;
    a treatment planning system for developing a noninvasive treatment plan for the arrhythmia based on the electrical potentials measured by the array of body surface electrodes and the heart-torso geometry obtained by the geometry determining device;
    a noninvasive means for treating the arrhythmia including implementing the noninvasive treatment plan developed by the treatment planning system; and
    an imaging processor configured to compute heart electrical activity data and generate an image of the heart from the electrical potentials measured by the array of body surface electrodes and the heart-torso geometry obtained by the geometry determining device,
    wherein:
        one of the noninvasive means for imaging the heart of the subject and identifying the arrhythmia or the treatment planning system further comprises a peripheral for defining an arrhythmia target from the image generated by the imaging processor; and
        the treatment planning system is further configured to:
            import the defined arrhythmia target as image data of the image data type generated by the geometry determining device; and
            register the imported image data to a primary planning dataset having the same image data type generated by the geometry determining device.

2. The noninvasive system of claim 1, wherein the geometry determining device comprises one or more of magnetic resonance imaging, X-ray, ultrasonography, or computed tomography.

3. The noninvasive system of claim 1, wherein the noninvasive means for treating the arrhythmia comprises stereotactic body radiotherapy, stereotactic ablative radiotherapy, stereotactic radiosurgery, fractionated radiotherapy, hypofractionated radiotherapy, high-frequency/focused ultrasound, or lasers.

4. The noninvasive system of claim 1, wherein the treatment planning system is digital imaging and communications in medicine (DICOM) compliant.

5. The noninvasive system of claim 4, wherein the treatment planning system further comprises a processor for importing DICOM compliant images and arrhythmia target information into the treatment planning system.

6. The noninvasive system of claim 1, wherein the noninvasive means for treating the arrhythmia further comprises a source of radiation operatively linked to a radiotherapy delivery unit; wherein the radiotherapy delivery unit comprises a processor for coordinating movement of the radiotherapy delivery unit with an image generated by the noninvasive means for imaging the heart of the subject and identifying the arrhythmia.

7. The noninvasive system of claim 1, further comprising a processor for converting the defined arrhythmia target into image data of the type generated by the geometry determining device.

8. The noninvasive system of claim 7, wherein the processor for converting the defined arrhythmia target into image data of the type generated by the geometry determining device is configured to convert the defined arrhythmia target into a format that can be imported into a digital imaging and communications in medicine (DICOM} compliant treatment planning system.

9. The noninvasive system of claim 8, wherein the processor for converting the defined arrhythmia target into DICOM compliant format further provides structure and dose data.

* * * * *

UNITED STATES PATENT AND TRADEMARK OFFICE
CERTIFICATE OF CORRECTION

| | | |
|---|---|---|
| PATENT NO. | : 11,406,845 B2 | Page 1 of 1 |
| APPLICATION NO. | : 15/773415 | |
| DATED | : August 9, 2022 | |
| INVENTOR(S) | : Clifford G. Robinson et al. | |

It is certified that error appears in the above-identified patent and that said Letters Patent is hereby corrected as shown below:

In the Specification

Column 1, Lines 12-15, delete "This invention was made with government support under NIH R01 HL03334331 Awarded by the National Institutes of Health. The government has certain rights in the invention.".

Signed and Sealed this
Twentieth Day of December, 2022

*Katherine Kelly Vidal*

Katherine Kelly Vidal
*Director of the United States Patent and Trademark Office*